(12) United States Patent
Ladebeck

(10) Patent No.: US 8,278,926 B2
(45) Date of Patent: Oct. 2, 2012

(54) METHOD FOR DETERMINING ATTENUATION VALUES OF AN OBJECT

(75) Inventor: Ralf Ladebeck, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 456 days.

(21) Appl. No.: 12/458,368

(22) Filed: Jul. 9, 2009

(65) Prior Publication Data

US 2010/0007346 A1    Jan. 14, 2010

(30) Foreign Application Priority Data

Jul. 10, 2008    (DE) .......................... 10 2008 032 479

(51) Int. Cl.
*G01V 3/00*    (2006.01)
(52) U.S. Cl. ..................................................... 324/309
(58) Field of Classification Search .......... 324/300–322; 600/410–435
See application file for complete search history.

(56) References Cited

U.S. PATENT DOCUMENTS

| | | | | |
|---|---|---|---|---|
| 5,345,381 A | * | 9/1994 | Wallschlaeger | 378/15 |
| 6,081,577 A | * | 6/2000 | Webber | 378/23 |
| 6,310,968 B1 | * | 10/2001 | Hawkins et al. | 382/131 |
| 6,339,652 B1 | * | 1/2002 | Hawkins et al. | 382/131 |
| 6,549,607 B1 | * | 4/2003 | Webber | 378/8 |
| 6,801,597 B2 | * | 10/2004 | Webber | 378/62 |
| 7,428,322 B2 | * | 9/2008 | Ragsdale | 382/128 |
| 7,609,808 B2 | * | 10/2009 | Tornai et al. | 378/63 |
| 7,889,902 B2 | * | 2/2011 | Zhang et al. | 382/128 |

FOREIGN PATENT DOCUMENTS

| | | |
|---|---|---|
| DE | 102005015070 A1 | 10/2006 |
| EP | 1788410 A1 | 5/2007 |

OTHER PUBLICATIONS

Haval Kadhem et al: "Ultra Low Dose CT Attenuation Correction Maps for Emission Computed Tomography", IEEE Nuclear Science Symposium Conference Record, Oct. 29-Nov. 1, 2006, vol. 4, p. 2123-2127; 2006.

* cited by examiner

*Primary Examiner* — Dixomara Vargas
(74) *Attorney, Agent, or Firm* — Harness, Dickey & Pierce, P.L.C.

(57) ABSTRACT

A method for determining attenuation values of an object is disclosed. In at least one embodiment, the method includes stationary positioning of the object, irradiation of the object via a radiation source, measurement of the object's transmission data via a detection system, determination of at least one geometric property of the object on the basis of the transmission data, and assignment of attenuation values to the object on the basis of the geometric property.

11 Claims, 3 Drawing Sheets

METHOD FOR DETERMINING ATTENUATION VALUES OF AN OBJECT

PRIORITY STATEMENT

The present application hereby claims priority under 35 U.S.C. §119 on German patent application number DE 10 2008 032 479.5 filed Jul. 10, 2008, the entire contents of which are hereby incorporated herein by reference.

FIELD

At least one embodiment of the present invention generally relates to a method for determining attenuation values of an object and to a magnetic resonance scanner.

BACKGROUND

Positron emission tomography (PET) is becoming increasingly widely established alongside magnetic resonance tomography (MR) in medical diagnostics. While MR is an imaging method for representing structures and slices inside the body, PET allows in vivo visualization and quantification of metabolic activities.

PET uses the special properties of positron emitters and positron annihilation in order to quantitatively determine the function of organs or cell regions. With this technique, appropriate radiopharmaceuticals marked with radionuclides are administered to the patient prior to the examination. As they decay, the radionuclides emit positrons which after a short distance interact with an electron, causing what is termed annihilation to occur. This results in two gamma quanta which fly apart in opposite directions (offset by 180°). The gamma quanta are detected by two opposing PET detector modules within a specific time window (coincidence measurement), as a result of which the annihilation site is localized to a position on the line connecting said two detector modules.

In the case of PET, the detector module must generally cover a greater part of the gantry arc length for the purpose of detection. It is subdivided into detector elements having a side length of a few millimeters. On detecting a gamma quantum, each detector element generates an event record that specifies the time and the detection location, i.e. the corresponding detector element. This information is passed to a fast logic unit and compared. If two events coincide within a maximum time interval, it is assumed that a gamma decay process is taking place on the connecting line between the two associated detector elements. The PET image is reconstructed using a tomography algorithm, i.e. so-called back-projection.

It is known to combine PET with other tomographic methods, in particular computed tomography. In combined PET/CT scanners it is possible, for example, to compensate for the lack of spatial resolution of PET systems. At the same time CT provides a visualization of the patient's anatomy, so that when the CT and PET data are mutually superimposed it is possible to establish precisely where in the body the PET activity occurred. In combined PET/CT scanners a PET scanner and CT scanner are typically arranged one behind the other such that the patient can be transferred seamlessly from one device to the other during an examination. The two measurements can then be performed in immediate succession.

It is advantageous to combine a PET scanner with an MR scanner because MR offers a higher soft tissue contrast than CT. Combined MR/PET systems are already known in which the PET detectors are arranged within an opening defined by the MR magnet together with the gradient system and excitation coil. In this arrangement they are positioned next to the excitation coil so that the target examination volumes of the MR and PET systems do not coincide but are offset in the z direction. Analogously to the PET/CT system it is consequently not possible here to measure PET and MR data simultaneously.

It is particularly preferred in this case for the PET scanner to be arranged inside the MR scanner and for the two examination volumes to be mutually superimposed. It will then be possible to acquire both morphological MR data and PET data during a single measurement pass. Apart from the time-saving effect, both image data sets can be presented in a simple manner, mutually superimposed so that a diagnosis will be made easier for the physician.

In order to integrate the PET scanner and MR scanner it is necessary to arrange the PET detectors inside the MR device so that the imaging volumes will be positioned isocentrically. For example, the PET detectors can be arranged on a support structure (support tube, gantry) located inside the MR device. These can consist of, for example, 60 detectors disposed in an annular arrangement on the support tube. A connected cooling means and electrical supply lines are required for each of the detectors, which can also be combined into detector blocks. These must likewise be arranged in the MR scanner. A number of signal processing units are additionally required that are likewise arranged in the MR scanner. Said units are connected to the detectors via the electrical supply lines and serve for signal processing.

In the case of a combination of MR and PET in a combined system, however, the gamma quanta are attenuated by anything situated between the site of origin of the respective gamma quanta and the PET detector. The attenuation must be taken into account in the reconstruction of PET images in order to prevent image artifacts. Situated between the site of origin of the gamma quantum in the patient's body and the acting PET detector are tissue within the patient's body as well as air, generally, and a part of the MR/PET system itself, for example a cover of the patient bore or a patient positioning table. The attenuation values of the components or accessory parts requiring to be taken into account are compiled into attenuation maps ($\mu$ maps). An attenuation map contains attenuation values for each volume element (voxel) of the volume under examination. Thus, for example, an attenuation map can be produced for the patient positioning table. The same applies to, for instance, local coils attached to the patient for MR examinations. In order to produce the attenuation map it is necessary to ascertain and combine the attenuation values. They can be ascertained by means of, for example, a CT recording or PET transmission measurement of the respective component. Attenuation maps of said kind can be measured on a once-only basis, since the attenuation values do not change over the life of the respective component. For the attenuation correction, great differences in the attenuation between the different tissues, especially air, soft parts and bone, are of primary importance.

It is known in the case of PET/CT systems to calculate an attenuation map from CT recordings using the X-ray absorption coefficients and use it to correct the attenuation of PET data. This can also be employed in measuring attenuation values of the components. It is not possible in the case of PET systems to ascertain the attenuation map directly from the actual measurement data. It must be measured in test measurements using homogeneous PET phantoms so that the intensity of the resulting gamma quanta will be known.

Methods are known by which attenuation values of the patient's body can be determined from anatomical MR images and can be added to the attenuation map. In this case special MR sequences are used by means of which bones, for example, can be identified. With the aid of the MR images it is then possible, based on knowledge of the position of the bones in the beam path of the gamma quanta, to appropriate attenuation values to the attenuation map.

However, the imaging volume of the MR scanner is generally not large enough for imaging the entire patient and thus providing attenuation values for the entire patient. Although it is possible in principle, by taking a plurality of measurements for example, to image the torso and the arms by means of MR and thereby determine the attenuation values, this requires an increased amount of time. It is also possible to increase the size of the imaging volume of the MR scanner by structural measures to such an extent that the entire anatomy of a patient can be recorded. Scanners of this type are extremely expensive, however. It is desirable to be able to determine attenuation values also for MR scanners having smaller imaging volumes.

SUMMARY

In at least one embodiment of the present invention, an improved method and/or a device is disclosed for determining attenuation values.

According to an example embodiment of the invention, a method for determining attenuation values of an object comprises:

Stationary positioning of the object,
irradiation of the object by means of a radiation source,
measurement of the object's transmission data by way of a detection system,
determination of at least one geometric property of the object on the basis of the transmission data, and
assignment of attenuation values to the object on the basis of the geometric property.

In this way it is possible to determine both attenuation values of objects that lie in the imaging volume of, for example, an MR/PET system and attenuation values of objects that lie outside the imaging volume. By way of the transmission measurement it is possible, for example, to produce an attenuation map in advance of an examination without protracted calibration. Attenuation values of the object are preferably determined for a subsequent PET examination. In this case it is advantageous to determine the geometric position and dimensions of the object and assign attenuation values at least approximately to the corresponding points in space.

In an advantageous embodiment of the invention, the detection system comprises a plurality of detectors. The geometric property of the object is a diameter and determining the diameter comprises the following method-related steps:

Comparison of the signal intensities of the detectors,
identification of the detectors which have detected radiation attenuated by the object on the basis of the signal intensity, and
determination of the diameter on the basis of the geometric position of the identified detectors and the beam path from the radiation source to the respective detector.

Because the position of the radiation source and the detectors relative to one another is known in the case of a rigid arrangement of the system, the beam path from the radiation source to the respective detector can easily be determined. It is therefore possible to identify, from the comparison of the measured signal intensities of the detectors, between which detectors and the radiation source the object lies. If the object is located for example on a patient positioning table, its position can be determined even more precisely. In PET systems a plurality of PET detectors are generally disposed in an annular arrangement around a patient bore. In said arrangement the PET detectors are comparatively small, so that a plurality of the PET detectors will usually detect radiation of the radiation source that has been attenuated due to objects in the beam path. It can easily be ascertained which of the detectors detects attenuated radiation and which of the detectors the radiation reaches without being attenuated. Both the position of the object located in the beam path and its size can be determined from the number of detectors positioned adjacent to one another.

In an advantageous embodiment of the invention, the assigning of attenuation values to the object comprises the following method-related steps:

Determination of at least one material contained in the object,
determination of attenuation values of the at least one material, and
assignment of the determined attenuation values to the object.

As the objects located in the beam path during an examination are generally known, the material contained in the object can be identified comparatively easily in advance. Attenuation values of the candidate materials can similarly be determined in advance and stored in a database, for example. Thus, following identifications of the geometric properties, the attenuation values can easily be assigned assuming the corresponding object is known.

It is advantageous if the assigned attenuation values of the object are added to an attenuation map that already contains attenuation values of other objects. In this way, when a plurality of transmission measurements of different objects are performed, an attenuation map can be built up for a subsequent examination.

In an advantageous embodiment of the method, the object is a patient's arm. In particular during examinations by way of combined MR/PET systems the arms of the patient often lie outside the imaging volume, which means that it is only possible to determine the attenuation values of the arms with the aid of an MR measurement, with a consequent increase in the amount of time and effort required. It is therefore particularly preferred if the arms of the patient are irradiated by means of the radiation source and in this way their position and their diameter, and therefore their attenuation values, can be determined immediately prior to a subsequent MR/PET measurement. In general it is possible to determine a geometric property of that part of the object which is not contained in the imaging volume of the MR system as the geometric property.

The device-related object is achieved by way of a magnetic resonance scanner having a PET unit, the PET unit comprising a plurality of detectors which are arranged around a patient bore. A radiation source is provided by means of which the objects inside the patient bore can be irradiated, the radiation being detectable by means of the detectors. By installing a radiation source inside the MR scanner the detectors of the PET unit can be used for transmission measurements of objects located in the patient bore and attenuation values of the objects determined thereby.

Preferably the MR/PET system has a computer unit which is embodied for processing the transmission data and by which the at least one geometric property of the object can be determined. The attenuation values of the objects can be determined by means of the computer unit.

In an advantageous embodiment of the invention the radiation source is embodied such that it emits gamma quanta. These can be detected immediately by means of the detectors of the PET unit. Providing a radioactive radiation source is therefore particularly preferred.

One embodiment of the invention is advantageous in that the radiation source is arranged inside the patient bore above a patient examination table. Since the attenuating objects are generally situated on the patient examination table, the transmission measurement can be performed particularly easily with a radiation source arranged above the patient examination table. It is particularly preferred in this case if the radiation source is arranged inside an RF excitation coil.

In an advantageous embodiment of the invention, the radiation source is mounted in a movable manner. A shielding container is provided into which the radiation source can be relocated when not in use. It can thus be ensured in a simple manner that the actual PET measurement is not distorted due to the radiation source.

BRIEF DESCRIPTION OF THE DRAWINGS

Further advantages and embodiments of the invention will emerge from the example embodiments described below in conjunction with the figures, in which.

DETAILED DESCRIPTION OF THE EXAMPLE EMBODIMENTS

Figure 1:
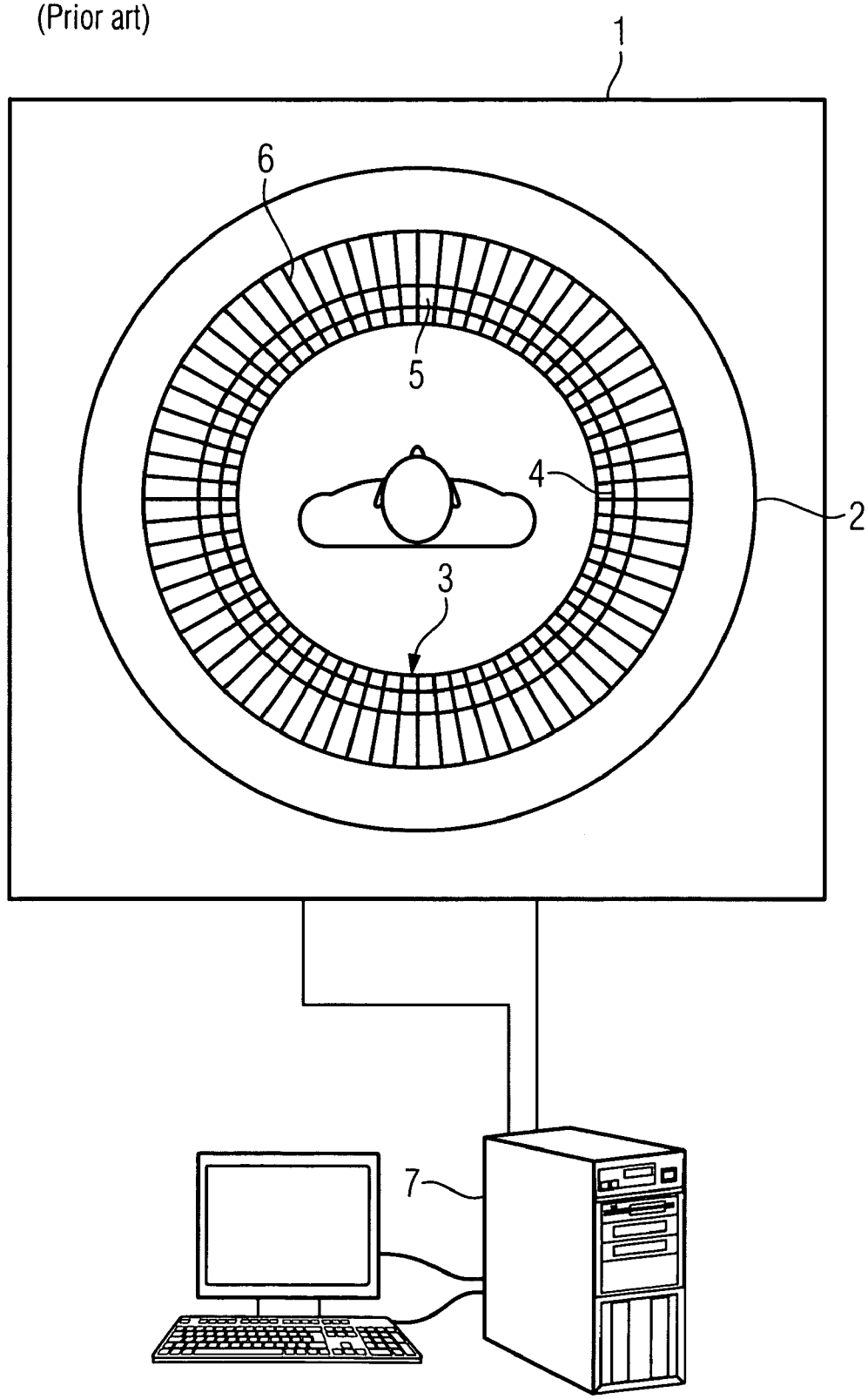
FIG. 1 is a schematic representation of an MR/PET scanner.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention can preferably be used with a combined MR/PET scanner. A combined device has the advantage that both MR and PET data can be acquired isocentrically. This enables the examination volume within the region of interest to be precisely defined using the data of the first modality (PET) and this information to be used in the other modality (e.g. magnetic resonance). Although it is possible to transfer the volume information relating to the region of interest from an external PET device to an MR device, an increased amount of time and effort is required for registering the data. For example, instead of the spectroscopy data, fMRI data, diffusion maps, T1- or T2-weighted images or quantitative parameter maps can also be acquired by means of magnetic resonance scans in the region of interest. Equally, computed tomography methods (e.g. perfusion measurement, multi-energy imaging) or X-rays can be used. What is advantageous about the described method in each case is that the region of interest can be narrowed down by means of the PET dataset very selectively to a specifically present pathology of the patient.

In addition, however, it is also possible, through use of a plurality of what are termed tracers, to represent different biological properties in the PET data set and thereby optimize still further the region of interest and the volume defined thereby, or to select a plurality of different target examination volumes at once, which are then analyzed in subsequent examinations.

FIG. 1 shows a known device 1 for superimposed MR and PET image representation. The device 1 consists of a known MR tube 2. The MR tube 2 defines a longitudinal direction z that extends orthogonally to the drawing plane of FIG. 1.

As shown in FIG. 1, a plurality of PET detection units 3 arranged in opposing pairs about the longitudinal direction z are disposed coaxially inside the MR tube 2. The PET detection units 3 preferably consist of an APD photodiode array 5 preceded by an array of LSO crystals 4 and an electrical amplifier circuit (AMP) 6. However, embodiments of the invention are not limited to the PET detection units 3 having the APD photodiode array 5 preceded by an array of LSO crystals 4, but other kinds of photodiodes, crystals and devices can equally be used for detection purposes.

Image processing for superimposed MR and PET image representation is performed by a computer 7.

Along its longitudinal direction z, the MR tube 2 defines a cylindrical first field of view. The plurality of PET detection units 3 define, along the longitudinal direction z, a cylindrical second field of view. According to an embodiment of the invention, the second field of view of the PET detection units 3 essentially coincides with the first field of view of the MR tube 2. This is implemented by appropriately adapting the arrangement density of the PET detection units 3 along the longitudinal direction z.

Figure 2:
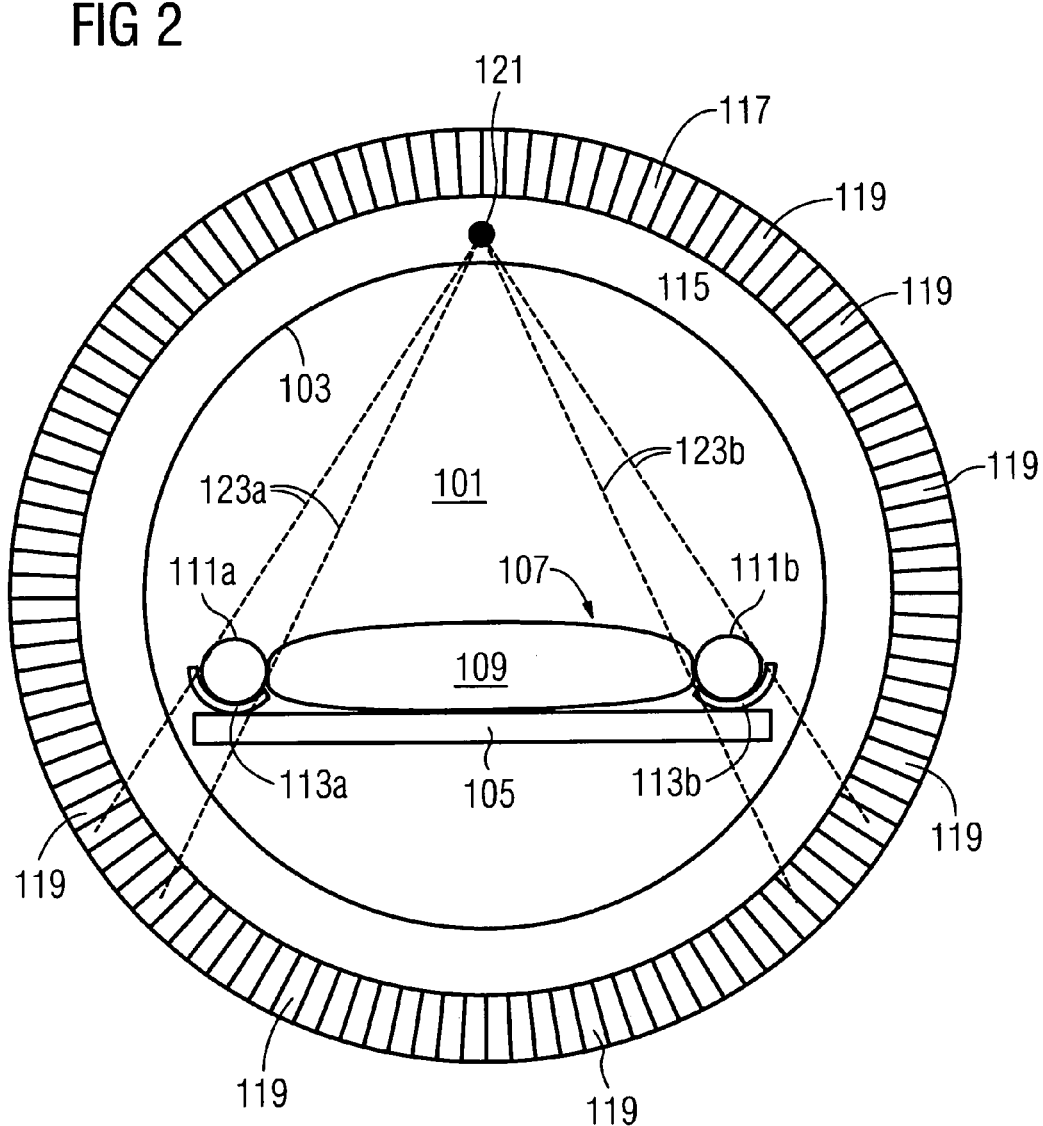
FIG. 2 is a schematic representation of an example embodiment of the invention.

FIG. 2 again shows a patient bore 101 of an MR/PET scanner in a sectional view. The patient bore 101 is defined by a patient tunnel 103. Arranged inside the patient bore 101 is a patient positioning table 105. Located on the patient positioning table 105 is a patient 107 whose torso 109 and arms 111a and 111b are shown in cross-section. The arms 111a and 111b of the patient 107 are positioned on the patient positioning table 105 in a stationary manner by means of positioning aids 113a and 113b. An RF excitation coil 115 and a PET detection system 117 are arranged outside the patient tunnel 103. The PET detection system 117 comprises a plurality of PET detectors 119. Arranged inside the HF excitation coil 115 is a radiation source 121.

In one embodiment variant of the invention, this emits gamma quanta. Alternatively it is possible to use an X-ray source. The gamma quanta emitted by the radiation source 121 strike the PET detectors 119 of the PET detection system 117 and are detected there. In the case of PET detectors 119 arranged in such a way that the gamma quanta from the radiation source 121 are not attenuated by an object located in the beam path, a first signal intensity results at the corresponding PET detectors 119.

With PET detectors 119 which detect gamma quanta attenuated by objects in the beam path, the corresponding signal intensity is less compared with the first signal intensity. This is shown by way of example in FIG. 2 by way of two pairs of beam paths 123a and 123b. The gamma quanta of the depicted beam paths 123a and 123b are attenuated by the arms 111a and 111b of the patient 107, the positioning aids 113a and 113b and the patient positioning table 105 before they strike the corresponding PET detectors 119.

By comparing the signal intensities of the PET detectors 119 it is possible to determine those PET detectors 119 which have detected gamma quanta attenuated by the arms 111a and 111b of the patient 107. Based on knowledge of said PET detectors 119 and knowledge of their geometric position it is possible to determine the diameter and the position of the arms 111a and 111b. Based on the acquired data, attenuation values for gamma quanta are assigned to the corresponding points in space. In this the attenuation value of water, for example, can be used in an approximation. The soft part tissue contained in the arms has essentially the same attenuation properties as water. Alternatively it is possible to use averaged attenuation values which take account of the proportion of bone tissue in the arms. Thus, the attenuation values of arbitrary objects inside the patient bore 101 can be merged to form an attenuation map which can then be used in the course of a following PET examination for attenuation correction of the measured PET data.

It is also possible to determine the inner limit of the arms 111a and 111b by means of an MR image of the torso 109 of the patient 107 and only the outer limit of the arms 111a and 111b of the patient 107 from the transmission measurement. The diameter and the position of the arms 111a and 111b are then also known, so that attenuation values can be assigned accordingly. By means of the positioning aids 113a and 113b used the arms 111a and 111b can be fixed in such a way that a sufficiently precise attenuation map can be determined.

In the assignment of the attenuation values to the arms 111a and 111b of the patient 107, the arm is assumed to be an approximately cylindrical object having previously determined attenuation values of the corresponding material, i.e. water for example, in the position defined by the positioning aids 113a and 113b. In this case the diameter of the corresponding cylinder can be acquired directly of transmission measurements or the combination of transmission measurements with the MR image. In the latter case the requirement in respect of the quality of the projection measurement can be reduced, resulting in a lower radiation exposure of the patient and a shorter measurement time.

It is also possible to improve the geometric resolution of the projection measurement by performing a second measurement with a slightly displaced radiation source.

Figure 3:
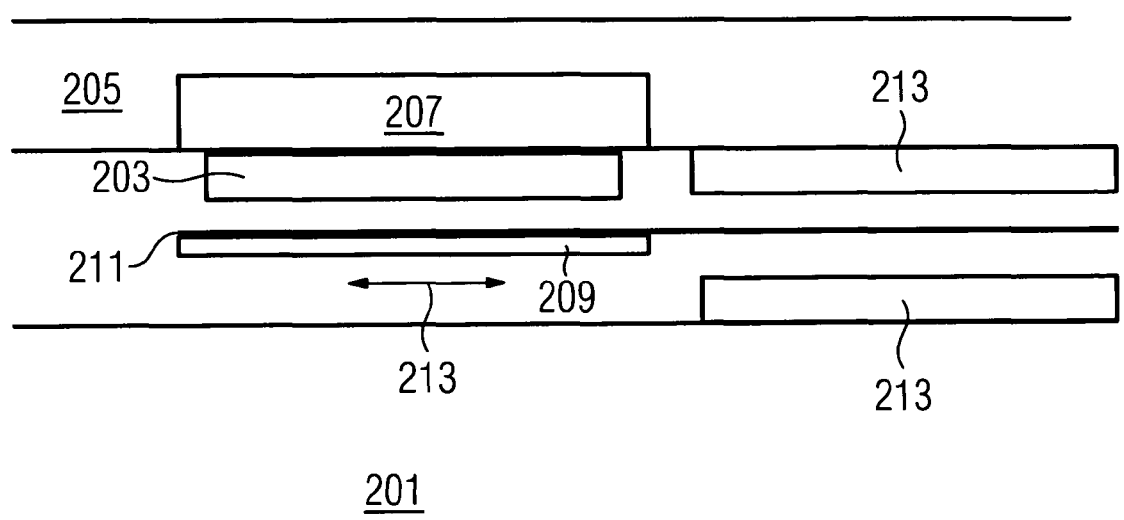
FIG. 3 is a schematic representation of a movable radiation source.

FIG. 3 shows the upper part of an MR/PET according to an example embodiment variant of the invention in a longitudinal section. Only the part of an RF excitation coil 203 and a PET detection system 205 located above a patient bore 201 is shown. A PET detector 207 of the PET detection system 205 is also shown. A radiation source 209 is arranged inside the HF excitation coil 203. The radiation source 209 is movably mounted on a runner rail 211 in the longitudinal direction. The direction of movement of the radiation source 209 is symbolized by the double arrow 213. Lead shields 213 are arranged offset in the longitudinal direction. In the position shown, the radiation source 209 is arranged in such a way that the gamma quanta emitted by it can be detected by the PET detectors 207 which are arranged annularly around the patient bore 201. However, as this would lead to measurement errors in the case of a PET scan of a patient, following the determination of attenuation values the radiation source 209 is moved along the runner rail 211 between the lead shields 213. As a result the gamma quanta emitted by it are shielded and no longer reach the PET detectors 207. A distortion of PET examinations is therefore precluded.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining attenuation values of an object using a medical imaging scanner, the method comprising:
   stationaryily positioning the object;
   irradiating the object using a radiation source;
   measuring transmission data of the object via a detection system of the medical scanner;
   determining at least one geometric property of the object on the basis of the measured transmission data; and
   assigning attenuation values to the object on the basis of the at least one determined geometric property.

2. The method as claimed in claim 1, wherein the detection system comprises a plurality of detectors and the geometric property is a diameter of the object, the determination of the diameter comprising:
   comparing signal intensities of the detectors;
   identifying the detectors which have detected radiation attenuated by the object on the basis of the signal intensity; and
   determining the diameter on the basis of the geometric position of the identified detectors and the beam path from the radiation source to the respective detector.

3. The method as claimed in claim 2, wherein the assigning of attenuation values to the object comprises:
   determining at least one material contained in the object;
   determining attenuation values of the at least one material; and
   assigning the determined attenuation values to the object.

4. The method as claimed in claim 3, wherein the assigned attenuation values of the object are added to an attenuation map which already contains attenuation values of other objects.

5. The method as claimed in claim 2, wherein the assigned attenuation values of the object are added to an attenuation map which already contains attenuation values of other objects.

6. The method as claimed in claim 1, wherein the assigning of attenuation values to the object comprises:
   determining at least one material contained in the object;
   determining attenuation values of the at least one material; and
   assigning the determined attenuation values to the object.

7. The method as claimed in claim 6, wherein the assigned attenuation values of the object are added to an attenuation map which already contains attenuation values of other objects.

8. The method as claimed in claim 1, wherein the assigned attenuation values of the object are added to an attenuation map which already contains attenuation values of other objects.

9. The method as claimed in claim 1, wherein the object is an arm of a patient.

10. The method as claimed in claim 1, wherein the stationary positioning of the object is effected inside a patient bore of an MR/PET system.

11. The method as claimed in claim 1, wherein a positioning aid is used for stationary positioning.

* * * * *